United States Patent [19]

Rowland

[11] Patent Number: 4,609,348

[45] Date of Patent: Sep. 2, 1986

[54] MOUTH AND CHEEK PROTECTOR

[75] Inventor: Arlene N. Rowland, Naples, Fla.

[73] Assignee: James R. Rehak, Naples, Fla.

[21] Appl. No.: 754,279

[22] Filed: Jul. 12, 1985

[51] Int. Cl.⁴ .............................................. A61C 7/00
[52] U.S. Cl. ...................................................... 433/2
[58] Field of Search ......................... 433/2, 6; 128/136

[56] References Cited

U.S. PATENT DOCUMENTS

| | | | |
|---|---|---|---|
| 2,627,268 | 2/1953 | Leppich | 128/136 |
| 2,653,600 | 9/1953 | Herman | 128/136 |
| 3,295,519 | 1/1967 | Gerber | 128/136 |
| 3,307,539 | 3/1967 | Petersen | 433/6 |
| 3,327,580 | 6/1967 | Herweg | 433/6 |
| 3,468,030 | 9/1969 | Peyser et al. | 32/34 |
| 3,844,286 | 10/1974 | Cowen | 128/136 |
| 3,943,924 | 3/1976 | Kallestad et al. | 128/136 |
| 4,180,912 | 1/1980 | Kesling | 433/14 |
| 4,512,740 | 4/1985 | Kurz | 433/6 |

Primary Examiner—Robert Peshock
Attorney, Agent, or Firm—Merrill N. Johnson

[57] ABSTRACT

The mouth and cheek protector is designed for use by persons undergoing orthodontal or orthognathic procedures requiring braces on the teeth. The protector consists of a thin strip of sponge-like cellular material formed to fit into the mouth and lie between the braces and the line of joinder between the gum and inner cheek. The cells of the sponge-like material have a generally uniform diameter of from 1/64th to 1/32nd of an inch. The major portion of the strip is approximately ⅛th of an inch thick with its opposite ends tapered to a thickness of 1/16th of an inch. One edge of the strip is straight and the opposite ends of the other edge are curved. The height of the strip is approximately ⅜ths of an inch and its length varies from one to two inches. In use, the curved edge of one or more of the strips rests against the braces and the straight edge lies close to and parallel with the line of joinder between the gum and inner cheek.

7 Claims, 6 Drawing Figures

MOUTH AND CHEEK PROTECTOR

BACKGROUND AND SUMMARY OF THE INVENTION

My invention relates to devices for protecting the mouth and inner cheeks of a person wearing braces on their teeth while undergoing orthodontal or orthognathic procedures.

One of the most disagreeable and painful aspects of orthodontal procedures and orthognathic surgery is the often painful and prolonged irritation of the inner surface of the mouth and cheeks caused by contact with the archwires, archbars, brackets and other metallic elements collectively called braces affixed to the teeth.

For many years the most widely used material for protecting the mouth and cheeks of persons wearing braces on their teeth has been a wax which is commonly supplied in the form of a pliable elongated cylinder or tube. Approximately one inch lengths of this wax are inserted into the mouth just above or below the braces to form a "cushion" intended to prevent the archwires and other metallic elements of the braces from coming into irritating contact with the adjacent surfaces of the mouth and cheeks.

However, as a person who recently underwent orthognathic surgery, I found that the conventional wax given me provided almost no relief from the constant irritation to my mouth and cheeks caused by the metallic elements of my braces. Nothing suggested by my doctors seemed to bring any relief until I began experimenting with strips of sponge-like material which I formed to fit into my mouth and lie between the braces and the area where the gum joins the inner surface of the cheek.

I found that by proper sizing and shaping of the strip, it would stay quite firmly in place for extended periods of time and act to prevent the irritating contact between elements of my braces and the inner surfaces of my mouth and cheeks. For best results, I found it desirable to use one protective strip over the front teeth and a separate strip on each side to protect the right and left cheeks.

My first protective strips were made of cellulose sponge which worked but had a tendency to deteriorate under long term usage. I have found the best material to have a generally uniform cell diameter of from 1/64th to 1/32nd of an inch. The strip may be either open or closed cell and the material may be cellulose, polystyrene, polyurethane or any one of a number of related thermoplastic foamed resins. For cosmetic purposes, the strips should be flesh colored.

DETAILED DESCRIPTION OF THE PREFERRED EMBODIMENTS

Figure 1:
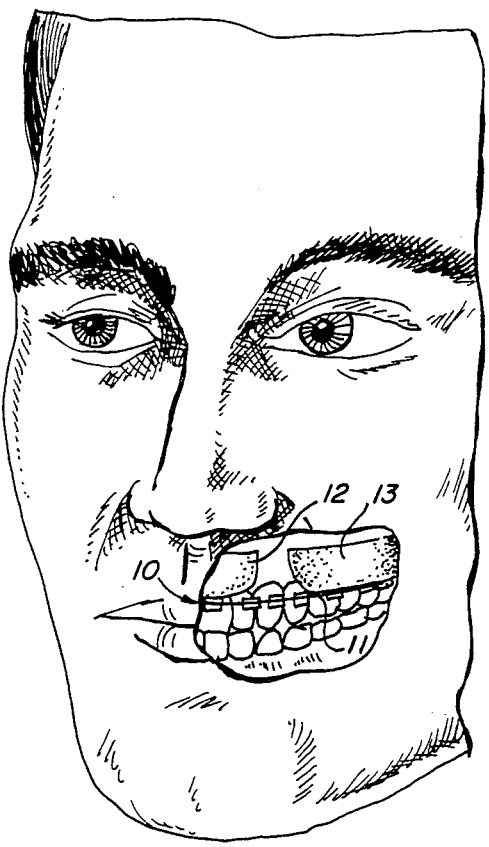
FIG. 1 is a perspective view of a person wearing braces on his upper teeth partially cut away to show the location of two of my mouth and cheek protectors.

Referring to the drawings in which similar numerals represent corresponding parts in each of the six figures, FIG. 1 shows a person wearing braces 10 on his upper teeth 11 with one of my mouth and cheek protectors 12 positioned over the person's front teeth and a second mouth and cheek protector 13 positioned over the person's cuspid and bicuspid teeth.

Figure 2:
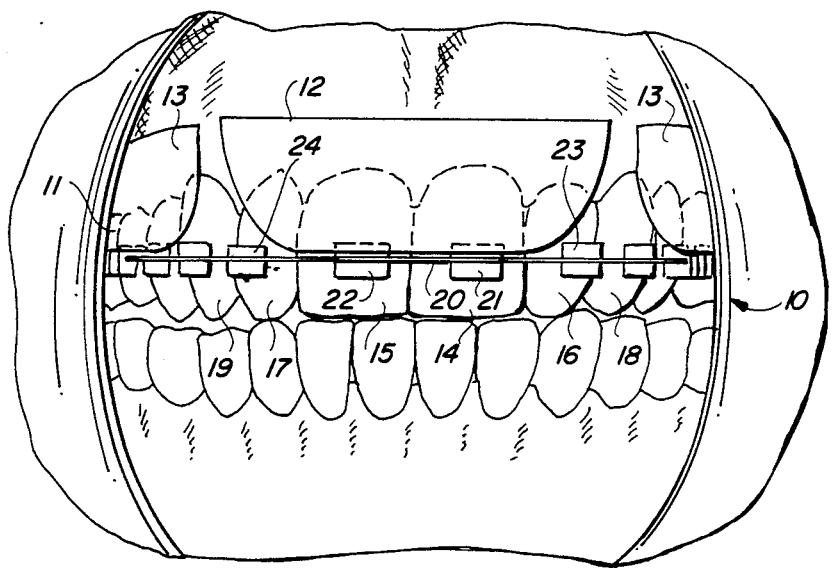
FIG. 2 is a detailed front view of an open mouth showing three of my mouth and cheek protectors in relation to braces on the upper teeth.

FIG. 2 provides a more detailed view of the preferred position of protectors 12 and 13 in the mouth in relation to braces 10, which in FIG. 2 consist of an archwire 20 connected to brackets 21, 22, 23, 24 and other brackets not numbered. Bracket 21 is affixed to the upper left central incisor 14. Bracket 22 is affixed to upper right central incisor 15. Bracket 23 is affixed to upper left lateral incisor 16 and bracket 24 is affixed to upper right lateral incisor 17. Similar brackets (unnumbered) are affixed to the upper left and right cuspids and bicuspids as shown in FIG. 2.

To protect the inside of the mouth beneath the nose from irritating contact with archwire 20 and brackets 21, 22, 23 and 24, protector 12 approximately 1⅝ths of an inch in length is inserted into the mouth directly over brackets 21 and 22 on incisors 14 and 15 with edge 12b of the protector between its curved ends 12c resting upon the braces 10 with the straight edge 12a lying close to and parallel to the line of joinder between the gum and inner surface of the lip or cheek.

In a similar manner, to protect the inside of the right and left cheeks from irritating contact with archwire 20 and the brace brackets on the upper cuspids and bicuspids shown in FIG. 2, two identical protectors 13 approximately 1¼ths of an inch in length are inserted directly over the brackets affixed to the cuspids and bicuspids as best shown in FIG. 2. The center portion of curved edge 13b rests on the archwire 20 and/or the brackets of braces 10 while the straight edge 13a of the protector lies generally parallel to the line of joinder between the upper gum and the inside surface of the cheek.

When protectors 12 and 13 are properly sized and shaped and positioned as shown and just described, I have found the protectors will stay firmly in place for hours at a time and serve to prevent irritating contact between the elements of the braces and the inner surfaces of the mouth and cheeks.

Preferably protectors 12 and 13 are thin strips of sponge-like cellular material whose cells have a generally uniform diameter of from 1/64ths to 1/32nd of an inch. The strip may be made of cellulose, polyurethane or a related thermoplastic foamed resin. However, I prefer strips made of polyurethane. For cosmetic reasons, the strips are preferably flesh colored.

Figure 3:
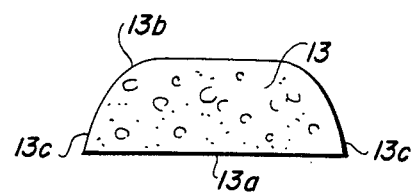
FIG. 3 is a front elevational view of a preferred embodiment of my mouth and cheek protector.
Figure 4:
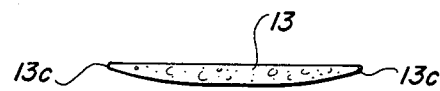
FIG. 4 is a plan view taken from above of the protector shown in FIG. 3.
Figure 5:
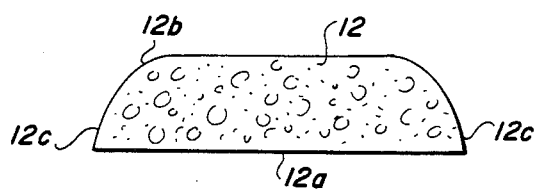
FIG. 5 is a front elevational view of a second preferred embodiment of my mouth and cheek protector.
Figure 6:
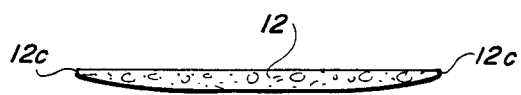
FIG. 6 is a plan view taken from above of the protector shown in FIG. 5.

Protector 12 designed for the front teeth is 1⅝ths of an inch in length while protector 13 designed to protect the inside of the cheek is 1¼ths inches in length. As shown in FIGS. 3-6, except for their length, protectors 12 and 13 are generally similar in size and shape. Both have a thickness of approximately ⅛th of an inch throughout most of its length except that their curved ends are tapered from a thickness of ⅛th of an inch to 1/64th of an inch at opposite ends 12c and 13c as shown in FIGS. 4 and 6.

Both protectors 12 and 13 are approximately ⅜ths of an inch in height and both have one straight edge 12a and 13a and a second edge 12b and 13b. Edges 12b and 13b have a center section which is parallel to edge 12a and 13a but whose ends are curved to intersect edge 12a and 13a at opposite ends 12c and 13c as shown in FIGS. 3 and 5.

When protectors are made and used as herein shown and described, they can be worn without discomfort for considerable periods of time and serve to prevent irritating contact between the braces on the teeth and the inner surfaces of the mouth and cheeks. While I have shown and described the use of my mouth and cheek protectors in relation to braces on a set of upper teeth, it will be understood that they can be used with equally beneficial results in relation to braces on a set of lower teeth.

While two preferred embodiments of my invention have been shown and described, it will be apparent that modifications can be made without departing from the spirit and scope of my invention and it is intended that the invention be limited only by the scope of the following claims.

I claim:

1. A mouth and cheek protector for use in the mouth of a person having braces on his teeth comprising a thin elongated strip of sponge-like cellular material having the following characteristics:
    (a) the cells of the sponge-like material have a generally uniform diameter of from 1/16th to 1/32nd of an inch,
    (b) the major central portion of the strip has a thickness of approximately ⅛th of an inch with its opposite ends tapered to a thickness of 1/16th of an inch,
    (c) the height of the strip is approximately ⅜ths of an inch, and
    (d) one elongated edge of the strip is straight and the opposite ends of the other elongated edge of the strip are curved to intersect said straight edge.

2. A mouth and cheek protector as set forth in claim 1 in which the sponge-like cellular material is a polyurethane.

3. A mouth and cheek protector as set forth in claim 1 in which the length of the protector is 1⅞ths of an inch.

4. A mouth and cheek protector as set forth in claim 1 in which the length of the protector is 1¼ths of an inch.

5. A mouth and cheek protector for use in the mouth of a person wearing braces on his teeth comprising a thin strip of sponge-like cellular material having the following characteristics:
    (a) the major central portion of the strip has a thickness of approximately ⅛th of an inch with its opposite ends tapered to a thickness of approximately 1/16th of an inch,
    (b) the height of the strip is approximately ⅜ths of an inch, and
    (c) the length of the strip is more than one inch and less than two inches.

6. A mouth and cheek protector as set forth in claim 5 wherein the cells of the cellular material have a generally uniform diameter of from 1/64th to 1/32nd of an inch.

7. A mouth and cheek protector as set forth in claim 5 wherein the cellular material is a polyurethane.

* * * * *